(12) United States Patent
Garris

(10) Patent No.: US 6,387,415 B1
(45) Date of Patent: *May 14, 2002

(54) SEQUESTERED METAL BIOCIDES USING IONIC POLYMERIC STABILIZING AGENTS

(75) Inventor: John P. Garris, Cumming, GA (US)

(73) Assignee: Bio-Lab, Inc., Decatur, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/973,295

(22) Filed: Apr. 1, 1998

Related U.S. Application Data

(63) Continuation-in-part of application No. 08/486,832, filed on Jun. 7, 1995, now Pat. No. 5,541,150.

(51) Int. Cl.$^7$ .......................... A01N 59/16; A01N 55/02
(52) U.S. Cl. .................... 424/618; 424/78.08; 424/630; 424/638; 424/641; 424/DIG. 6; 504/151; 504/152; 504/157; 504/158; 514/494; 514/495; 514/499; 514/500; 514/836
(58) Field of Search ................................. 514/492, 494, 514/495, 499, 500, 836; 424/617, 618, 630, 634, 635, 638, 641, 78.08, DIG. 6; 504/152, 157, 151, 158

(56) References Cited

U.S. PATENT DOCUMENTS

| | | | | | |
|---|---|---|---|---|---|
| 3,940,482 A | * | 2/1976 | Grand | ........................ | 514/188 |
| 4,020,200 A | * | 4/1977 | Groszek et al. | ............. | 427/416 |
| 4,324,578 A | | 4/1982 | Seymour et al. | | |
| 4,780,216 A | * | 10/1988 | Wojtowicz | .................. | 210/756 |
| 5,149,354 A | | 9/1992 | Delaney | | |
| 5,160,527 A | | 11/1992 | Law et al. | | |
| 5,171,350 A | * | 12/1992 | Stainer | ........................ | 504/121 |
| 5,242,685 A | * | 9/1993 | Ruppersberger et al. | .. | 424/78.26 |
| 5,284,844 A | * | 2/1994 | Lorenz et al. | ............ | 514/222.5 |
| 5,324,477 A | | 6/1994 | Schroeder et al. | | |
| 5,332,511 A | * | 7/1994 | Gay et al. | .................... | 210/755 |
| 5,541,150 A | * | 7/1996 | Garris | ........................ | 504/152 |

* cited by examiner

Primary Examiner—Jose' G. Dees
Assistant Examiner—Frank Choi
(74) Attorney, Agent, or Firm—Woodard, Emhardt, Naughton, Moriarty & McNett

(57) ABSTRACT

Metal-containing biocides for treating swimming pool water, spas, cooling towers, or other industrial applications without staining are disclosed. The biocidal compositions include a source of metal and a polymeric sequestering agent. The polymeric sequestering agent may be a water-soluble anionic or cationic polymer. Conventional sequestering agents may also be included in the composition.

22 Claims, 3 Drawing Sheets

SEQUESTERED METAL BIOCIDES USING IONIC POLYMERIC STABILIZING AGENTS

This application is a continuation-in-part of U.S. patent application Ser. No. 08/486,832 filed Jun. 7, 1995, now U.S. Pat. No. 5,541,150 issued Jul. 30, 1996.

FIELD OF THE INVENTION

The present invention relates generally to biocides for water systems such as swimming pools, spas, cooling towers, or other industrial applications, and more particularly to biocides using copper, silver or zinc as their active agent.

BACKGROUND OF THE INVENTION

Certain metals, such as copper, silver, zinc, etc., are known to possess biocidal qualities when used in circulating water systems. Unfortunately, many metal ions easily precipitate in alkaline or near-alkaline water conditions as insoluble salts of oxides, hydroxides, and/or carbonates, removing the metals from the system and thus removing the ability of the metal ion to act as a biocide.

In order to improve the efficacy of metals to act as biocides in water, sequestering agents, such as alkanolamines, aminocarboxylic acids or citric acid have been used to improve the stability of the metal in aqueous solutions conditions. These simple, organic compounds contain amine, hydroxyl, and carboxyl functionalities that exhibit sequestration capacity for polyvalent metal cations. Problems remain however, because alkanolamines, aminocarboxylic acids, and citric acid deteriorate quickly in the presence of halogens and other oxidizers, bacteria, sunlight or heat, thus allowing the metal to become unsequestered and subject to loss due to precipitation. The net result in pools, spas, cooling towers or other water systems is a loss of activity of the metal ions.

Another problem encountered in water treatment applications, such as swimming pools or spas, is that metals precipitate to form unsightly stains on the pool's surface. In particular, metal hydroxides, metal oxides and metal carbonates are known to cause unsightly stains that are difficult to remove.

A need therefore exists for a method of stabilizing soluble metals for longer periods of time during treatment and application, thereby increasing their effective life and preventing stains from occurring on swimming pool surfaces. The present invention addresses that need.

SUMMARY OF THE INVENTION

Briefly describing one aspect of the present invention there are provided metal-containing biocides for treating swimming pool water without staining the sides of the pool. The inventive biocidal compositions include a source of a metal such as copper, silver, zinc, etc., and a polymeric sequestering agent. The polymeric sequestering agent may be a water-soluble anionic polymer or a water-soluble cationic polymer. Conventional sequestering agents may also be included in the composition.

One object of the present invention is to provide metal-containing biocides that do not stain the solid surfaces of a swimming pool.

A second object of the present invention is to provide a metal-containing biocidal composition that maintains activity longer due to stabilization of metal ions in solution by polymeric sequesterants.

Further objects and advantages of the present invention will be apparent from the following description.

DESCRIPTION OF THE PREFERRED EMBODIMENT

Figure 1:
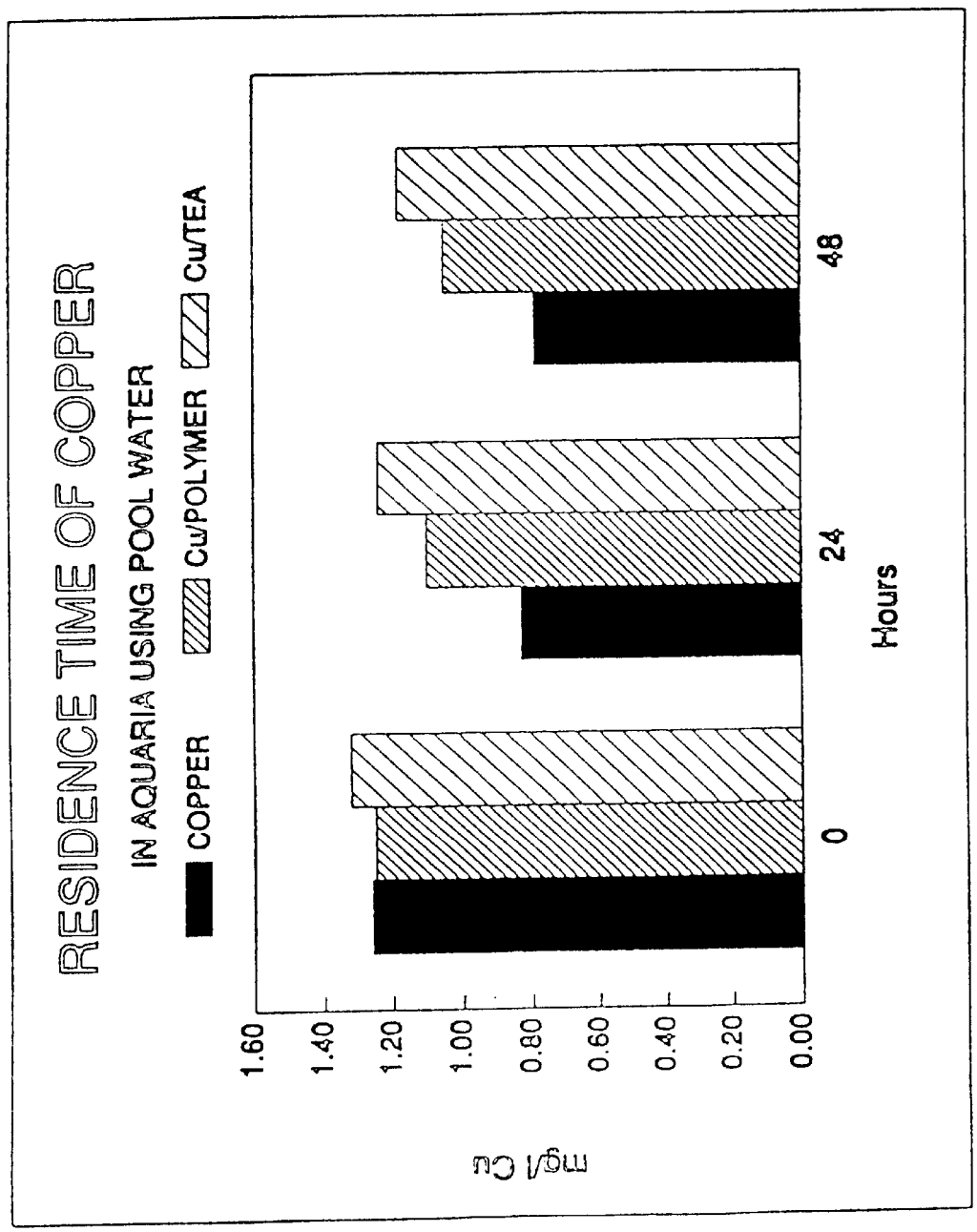
FIG. 1 shows the residence time of soluble copper, copper/polymer and copper triethanolamine using 28 liter aquaria (error bars equal to ± one std. deviation).

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the described device, and such further applications of the principles of the invention as illustrated therein being contemplated as would normally occur to one skilled in the art to which the invention relates.

As previously indicated, the invention relates to improved biocidal formulations for water treatment applications based on an improved method of stabilizing metals such as copper, silver, zinc, etc. The invention employs ionic polymeric stabilizing agents, preferably in conjunction with a conventional organic sequestering agent such as alpha-hydroxyacids and the like, to sequester elemental metal cations. This formulation stabilizes metals even in alkaline environments and prevents their loss due to precipitation, thereby increasing the effective life of the biocide and preventing staining of swimming pool surfaces.

In one aspect of the present invention the metal is provided as a soluble or insoluble metal salt such as metal acetates, metal chlorides, metal formates, metal nitrates, metal sulfates, or metal carbonates. The metal may also be present in its elemental form. The amount of metal salt present may vary from 0.01% to 99.9% by weight as a single metal salt or mixed metal salt composition. Preferably, the metal salt is present in an amount of about 1% to 40% by weight of the composition. The amount of elemental metal sequestered in the formulation may range from 0.01% to 30%, with 1% to 10% being preferred, and 3% to 8% being most preferred.

In some preferred embodiments, the invention uses water-soluble anionic polymers such as polyacrylic acid, polymethacrylic acid, polyvinyl sulfonic acid, polystyrene sulfonic acid, polymaleic acid, polyaspartic acid, polyphosphino carboxylic acids, copolymers, terpolymers, or tetrapolymers thereof or the sodium, potassium, calcium salts or metal salts of said polymers. In other preferred embodiments, water-soluble cationic polymers such as poly [oxyethylene-(dimethylimino) ethylene-(dimethylimino) ethylene dichloride], polyethylene imine, diallyl dimethyl ammonium chloride, polyacrylamide derivatives, polyamines, polyvinyl amine, chitosan, polyethylene. amine or a polymer of 1,6-hexanediamine-N,N,N',N'-tetramethyl or the fluoride, chloride, or bromide salts thereof, and the like are used. The amount of polymer or mixture of polymers present in the composition may vary from 0.01% to 99.9% by weight; however, 10% to 50% is preferred.

In some embodiments the water-soluble cationic polymer is a copolymer, terpolymer, or tetrapolymer of one or more of the water-soluble cationic polymers.

The molecular weight of the ionic polymeric agent is preferably between about 500 Da and 20,000,000 Da, with polymers having a molecular weight of between about 1,000 Da and 5,000,000 Da being more preferred, and polymers having a molecular weight of between about 1,000 Da and 1,500,000 Da being most preferred.

In one aspect of the invention, conventional organic sequestering agents are used with the polymeric agent. For example, hydroxy-carboxylic acids, aminocarboxylic acids, polyamines, alkanolamines, polyphosphates, phosphonic acids, crown ethers, amino acids, etc. may be used in conjunction with the polymeric agent as described below. In certain preferred embodiments organic acids such as, e.g., oxalic acid, suberic acid, acetic acid, tricarballic acid, succinic acid, malonic acid and maleic acid, and the salts thereof, are used. Especially preferred are the hydroxy-carboxylic acids such as, e.g, citric acid, gluconic acid, tartronic acid, lactic acid, tartaric acid, malic acid, glyceric acid, or tetrahydroxy succinic acid, and the salts thereof, and the lactone or ester forms of such acids. The organic aces and hydroxy-acids are preferred in certain embodiments because the other noted sequestering agents are sources of nitrogen and phosphorous, two critical nutrients for algae growth. These conventional sequestering agents are typically added to the composition at 0.01% to 99.9% by weight; however, 5% to 40% is preferred.

Optionally, other components like dyes, perfumes, stabilizers, etc. can be included in the formulas described herein.

EXAMPLE 1

Preparation of a Copper composition with an Anionic Polymer and a Conventional Organic Sequestering Agent Forty grams of a 50% solution of partially neutralized (10 to 50 percent) polyacrylic acid was combined with 25 grams of anhydrous citric acid, 15 grams of water and 20 grams of copper sulfate pentahydrate. This formulation was heated and stirred to allow the copper sulfate to go into solution. This formulation yields a thick royal blue liquid that contains 5.1% elemental copper. This example provides about 20 g polymer and about 5 g metal, for a polymer-to-metal ratio of about 4:1.

EXAMPLE 2

Preparation of a Copper Composition with an Anionic Polymer and a Conventional Organic Sequestering Agent Forty grams of a 50% solution of a copolymer of maleic anhydride and styrene sulfonate, 20 grams of glucono-deltalactone and 22 grams of copper acetate are heated and stirred with 18 grams of water to yield a very dark blue liquid formulation that contains 7.8% elemental copper. This example provides about 20 g polymer and about 7 g metal, for a polymer-to-metal ratio of about 3:1.

EXAMPLE 3

Preparation of a Copper composition with a cationic Polymer and a Conventional Sequestering Agent Thirty-five grams of ethylene-diamine tetraacetic acid disodium salt (EDTA) is reacted with 13.5 grams of copper carbonate and 41.5 grams water. Some carbon dioxide is released in this reaction. 30 grams of a 50% solution of a polymer of 1,6-hexanediamine-N,N,N',N'-tetramethyl chloride salt is added. This formulation will yield a thick blue liquid that contains 5.8% elemental copper. This example provides about 15 g polymer and about 7 g metal, for a polymer-to-metal ratio of about 3:1.

EXAMPLE 4

Preparation of a Copper Composition with an Anionic Polymer and a Conventional Organic Sequestering Agent Forty grams of a 40% solution of 2-Propenoic acid polymer with 2-hydroxy-3-(2-propenyloxy)-1-propanesulfonic acid monosodium salt (a copolymer of acrylic acid and an allyloxy, hydroxypropyl sulfonate), 20 grams of gluconodeltalactone and 28 grams of copper sulfate pentahydrate are heated and stirred with 8 grams of potassium hydroxide and 4grams of water to yield a very dark blue liquid formulation that contains 7.1% elemental copper. This example provides about 16 g polymer and about 7 g metal, for a polymer-to-metal ratio of about 2:1.

EXAMPLE 5

Preparation of a Copper Composition with an Anionic Polymer

Fifty grams of a 40% solution of 2-Propenoic acid polymer with 2-hydroxy-3-(2-propenyloxy)-1-propanesulfonic acid monosodium salt (a copolymer of acrylic acid and an allyloxy, hydroxypropyl sulfonate), 12 grams of hydrochloric acid and 25 grams of copper sulfate pentahydrate are heated and stirred with 13 grams of water to yield a very dark blue liquid formulation that contains 6.4% elemental copper. This example provides about 20 g polymer and about 6.25 g metal, for a polymer-to-metal ratio of about 3:1.

EXAMPLE 6

Preparation of a Copper Composition Containing a Mixture of High and Low Molecular Weight Polyanions and a Conventional Sequestering Agent Twenty-five grams of a 40% solution of 2-propenoic acid, polymer with 2-hydroxy-3-(2-propenyloxy)-1-propanesulfonic acid monosodium salt, a copolymer of acrylic acid and an allyloxy, hydroxypropyl sulfonate, 18 grams glucono-deltalactone, 15 grams of polyacrylic acid (molecular weight 1,000,000 to 1,500,000 Da) sold under the trade name (Aquatreat* AR-7H), 4grams potassium hydroxide and 26 grams of copper sulfate pentahydrate are heated and stirred with 12 grams of water to yield a very dark blue liquid formulation that contains 6.6% elemental copper. This example provides about 13 g polymer and about 6.5 g metal, for a polymer-to-metal ratio of about 2:1.

EXAMPLE 7

Preparation of a Dry Mixed Metal Composition Containing a Polymer Salt Combined with a Conventional Sequestering Agent Seventy-four and one-half grams of copper sulfate pentahydrate, 60 grams of citric acid, 60 grams of sodium polyacrylate, 5 grams of zinc sulfate, 1 gram of silver nitrate. This mixture is stirred using a dry component mixing device such as a V blender This mixture is packaged as is or compressed into a stick or puck to change the dissolution characteristics. This example provides about 57 g polymer and about 20.4 g metal, for a polymer-to-metal ratio of about 2.8:1.

EXAMPLE 8

Preparation of a Copper Composition with a High Molecular Weight Cationic Polymer and a Conventional Sequestering Agent Forty-two grams of triethanolamine is reacted with 28 grams of copper sulfate pentahydrate and 25 grams of water. Five grams of a dialyl dimethyl ammonium chloride high molecular weight cationic polymer is added to the formula. This formula gives a very dark blue solution containing 7.1% copper. This example provides about 5 g polymer and about 7 g metal, for a polymer-to-metal ratio of about 0.7:1.

EXAMPLE 9

Preparation of a Silver Composition with an Anionic Polymer

Fifteen grams of a 40% solution of 2-propenoic acid polymer with 2-hydroxy-3-(2-propenyloxy)-1-propanesulfonic acid monosodium salt (a copolymer of acrylic acid and an allyloxy, hydroxypropyl sulfonate), and 2 grams of silver nitrate are diluted in 83 grams of water to give a clear yellow solution that has 1.3% elemental silver. This example provides about 6 g polymer and about 1.3 g metal, for a polymer-to-metal ratio of about 4.7:1.

EXAMPLE 10

Preparation of a Zinc Composition with an Anionic Polymer and a Conventional Sequestering Agent Twenty grams of a 25% solution of salt (a copolymer of maleic anhydride and styrene sulfonate), 2 grams citric acid and 5 grams of zinc acetate are diluted in 80 grams of water to give a light yellow solution that has 1.8% elemental zinc. This example provides about 5 g polymer and about 1.5 g metal, for a polymer-to-metal ratio of about 3.4:1.

EXAMPLES 11–13

Biocidal Effectiveness

Minimum inhibitory concentration (MIC) laboratory studies were performed to demonstrate that the compositions of the present invention retained their biocidal efficacy. MIC data gives the minimum concentration of biocide needed to prevent growth of the algae in a culture.

The MIC studies are performed in sterile glassware using both viability and sterility controls. An algae suspension is added to test tubes containing the appropriate amounts of test biocide and the tubes are incubated for two weeks under fluorescent lights (on a "12 hour on"/"12 hour off" lighting regimen). The cultures are then measured by visual observation to determine the presence of living algae.

As seen in Examples 11–13, there was equivalent biocidal activity between free elemental copper as copper sulfate, copper complexed with triethanolamine ("TEA"), and the polymer sequestered copper at equivalent doses of active copper present against various blue-green and green algal species.

EXAMPLE 11

| MIC results against Phormidium sp. using various concentrations of copper. | | | | | |
|---|---|---|---|---|---|
| Copper Conc. (ppm) | 0.50 | 0.25 | 0.125 | 0.065 | 0.025 |
| Unsequestered Copper | – | – | – | – | – |
| TEA Sequestered Copper | – | – | – | – | – |
| Polymer Sequestered Copper | – | – | – | – | – |

(–) indicates no algae growth was seen
(+) indicates algae growth was seen

EXAMPLE 12

| MIC results against *Phormidium inudatum* using various concentrations of copper. | | | | | |
|---|---|---|---|---|---|
| Copper Conc. (ppm) | 3.0 | 1.0 | 0.5 | 0.25 | 0.125 |
| Unsequestered Copper | – | – | – | – | – |
| TEA Sequestered Copper | – | – | – | – | – |
| Polymer Sequestered Copper | – | – | – | – | – |

(–) indicates no algae growth was seen
(+) indicates algae growth was seen

EXAMPLE 13

| MIC results against Chlorella sp. using various concentrations of copper. | | | | | |
|---|---|---|---|---|---|
| Copper Conc. (ppm) | 10.0 | 9.0 | 8.0 | 7.0 | 6.0 |
| Unsequestered Copper | – | – | – | – | – |
| TEA Sequestered Copper | – | – | – | – | – |
| Polymer Sequestered Copper | – | – | – | – | + |

(–) indicates no algae growth was seen
(+) indicates algae growth was seen

EXAMPLE 14

Field Tests

Further tests were done using test swimming pools infested with algae. These pools were treated with either the polymer sequestered copper or copper triethanolamine at a concentration of 0.7 to 0.5 ppm. All the pools treated with the formulation of the invention killed the algae; however some of those pools treated with the copper triethanolamine complex failed to kill the algae. The polymer additive may, unexpectedly, effectively "deliver" the copper to the cell wall, thus bringing higher concentrations of the copper in closer contact with the cell. This may be a mechanism to explain the result because copper triethanolamine works by simple diffusion.

EXAMPLE 15

Residence Time of Cooper

Soluble elemental copper is easily removed from solution through filtration and by combining with carbonate, chloride or hydroxide ions that are commonly found in process water, such as swimming pools, spas or industrial water applications to form insoluble copper carbonates and hydroxides. Sequestered metals do not readily form these insoluble salts or filter out of the system. Thus, sequestered metals have a higher residence time in the water. This allows the metal to work for longer periods of time.

The residence time of copper was tested using a system of aquaria. Copper was tested in various sequestered forms and as free soluble copper. Initially, the copper concentration will be 1.25 ppm as $Cu^{++}$. Copper concentrations were tested photometrically using a HACH 3000 colorimeter.

Initial copper concentrations were tested 15 minutes after the addition of granular or liquid ingredients. Copper concentrations were checked at 24 hours and 48 hours. The volume of the aquarium is 28 liters. The experimental design tested a copper sulfate only control, a copper triethanolamine (TEA) complex, and the polymer-copper. See FIG. 1.

EXAMPLE 16

Residence Time in Field Tests

Figure 2:
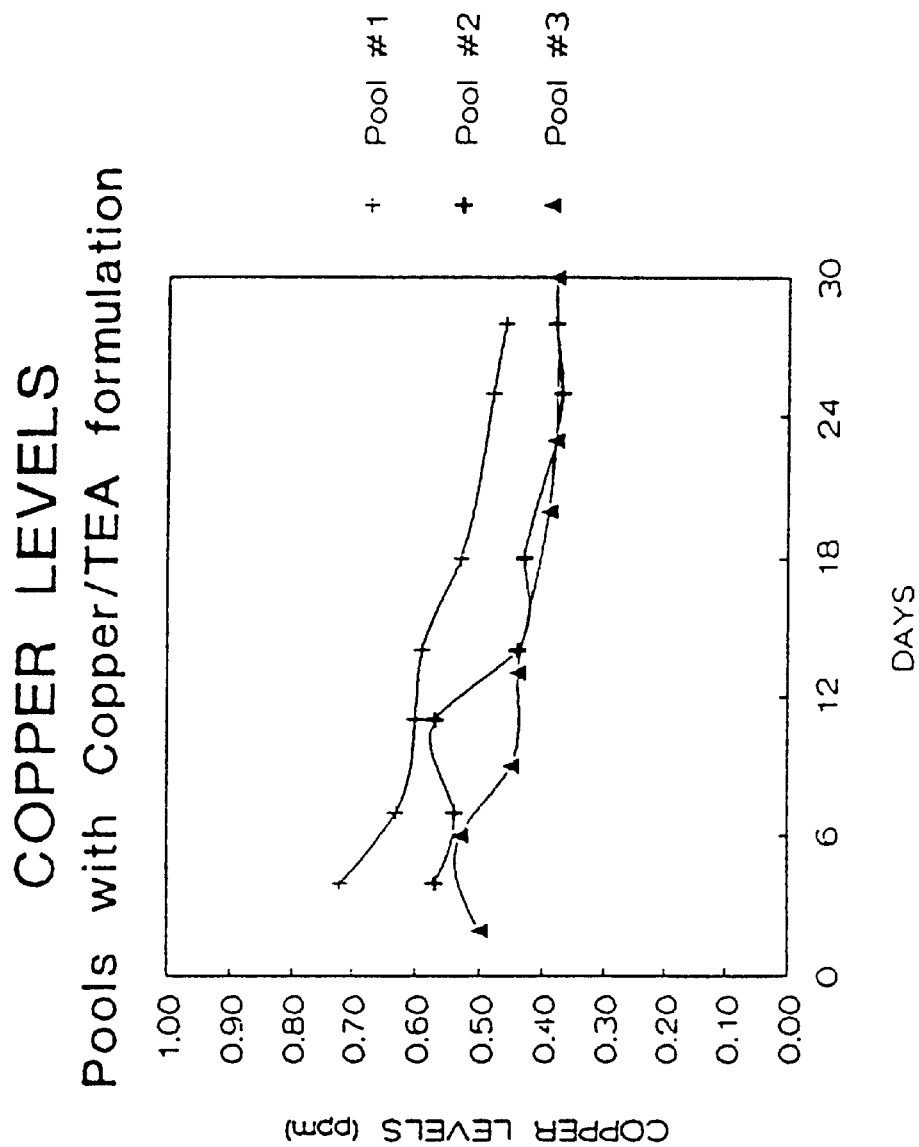
FIGS. 2 and 3 show equivalent residence times for those samples containing copper/TEA and copper/polymer formulations.
Figure 3:
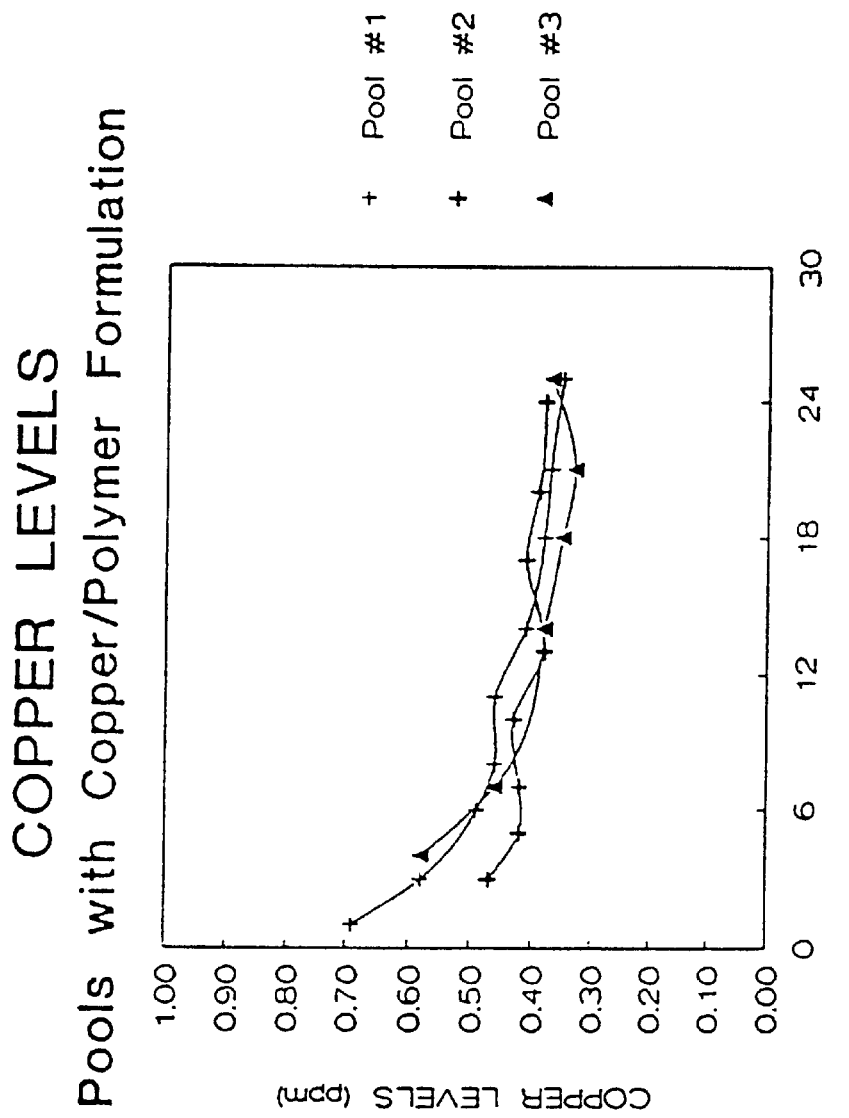

Residence times were tracked in field pools that were treated with either copper sequestered with TEA or copper sequestered with polymer. The tests show equivalent residence times for those samples containing copper/TEA and copper/polymer formulations. See FIGS. 2 & 3.

EXAMPLES 17–20

Biocidal Effectiveness

Minimum inhibitory concentration (MIC) laboratory studies were performed to demonstrate that the compositions of the present invention retained their biocidal efficacy. MIC data gives the minimum concentration of biocide needed to prevent growth of bacteria in a culture.

Individual MIC's were determined by screening on microtiter plates. In order to determine the MIC's, 50 μl of phosphate water is added to each row in columns 2–12. Next, 100 μl of a biocide is added to column 1 (A–H). Fifty microliters of the biocide is removed from column 1 and serially diluted from columns 2–11 using an eight tip pipettor (octapette). Finally, 50 μl of microbial inoculum is added to columns 1–11 (all rows) and column 12 (row A and E only). Column 12 serves as the row for sterility and viability controls.

Bacterial inoculua contain about $1 \times 10^9$ colony forming units (cfu) per ml are prepared in ⅕ strength Nutrient broth. Bacterial microtiter plates are incubated at 37° C. for 48 hours. MIC's are determined by visual observation of the plates.

As seen in Examples 17–20, there was equivalent biocidal activity between free elemental silver and the polymer sequestered silver at equivalent doses of active silver.

EXAMPLE 17

| MIC results against *E. Coli* using various concentrations of silver. | | | | | |
|---|---|---|---|---|---|
| Silver Conc. (ppm) | 25 | 12.5 | 3.1 | 1.56 | 0.39 |
| Unsequestered Silver | – | – | – | + | + |
| Polymer Sequestered Silver | – | – | – | + | + |

(–) indicates no bacterial growth was seen
(+) indicates bacterial growth was seen

EXAMPLE 18

| MIC results against *S. aureus* using various concentrations of silver. | | | | | |
|---|---|---|---|---|---|
| Silver Conc. (ppm) | 25 | 12.5 | 1.56 | 0.78 | 0.39 |
| Unsequestered Silver | – | – | – | + | + |
| Polymer Sequestered Silver | – | – | – | + | + |

(–) indicates no bacterial growth was seen
(+) indicates bacterial growth was seen

EXAMPLE 19

| MIC results against *E. Coli* using various concentrations of copper. | | | | | |
|---|---|---|---|---|---|
| Copper Conc. (ppm) | 50 | 25 | 12.5 | 1.56 | 0.78 |
| Unsequestered Copper | – | – | + | + | + |
| Polymer Sequestered Copper | – | – | + | + | + |

(–) indicates no bacterial growth was seen
(+) indicates bacterial growth was seen

EXAMPLE 20

| MIC results against *S. aureus* using various concentrations of copper. | | | | | |
|---|---|---|---|---|---|
| Copper Conc. (ppm) | 25 | 12.5 | 1.56 | 0.78 | 0.39 |
| Unsequestered Copper | – | – | – | + | + |
| Polymer Sequestered Copper | – | – | – | + | + |

(–) indicates no bacterial growth was seen
(+) indicates bacterial growth was seen While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of reducing the ability of a copper-, silver-, and/or zinc-containing biocide to stain pool surfaces, said method comprising providing the copper-, silver-, and/or zinc-containing biocide to a pool in conjunction with a water-soluble anionic or cationic polymeric sequestering agent effective to sequester at least some of the copper, silver, and/or zinc; wherein the copper, silver, and/or zinc provided by the biocide is present in the pool water in an amount ranging from 0.025 ppm to 0.7 ppm, and the ratio of anionic or cationic polymeric sequestering agent to copper, silver, and/or zinc in the pool water is between 0.7:1 and 4.7:1.

2. The method of claim 1 wherein said water-soluble anionic or cationic polymeric sequestering agent is a water-soluble anionic polymer.

3. The method of claim 2 wherein said water-soluble anionic or cationic polymeric sequestering agent is a member selected from the group consisting of polyacrylic acid, polymethacrylic acid, polyvinyl sulfonic acid, polystyrene sulfonic acids, polymaleic acid, polyaspartic acid and polyphosphino carboxylic acid.

4. The method of claim 2 wherein said water-soluble anionic polymer is a copolymer, terpolymer, or tetrapolymer of one or more water-soluble anionic polymers.

5. The method of claim 2 wherein said water-soluble anionic polymer is provided as a salt.

6. The method of claim 1 wherein said water-soluble anionic or cationic polymeric sequestering agent is a water-soluble cationic polymer.

7. The method of claim 6 wherein said water-soluble cationic polymer is a member selected from the group consisting of polyoxyethylene-(dimethylimino) ethylene-(dimethylimino) ethylene dichloride], polyethylene imine, diallyl dimethyl ammonium chloride, polyacrylamide derivatives, polyamines, polyvinyl amine, chitosan, polyethylene amine, polymers of 1,6-hexanediamine-N,N,N',N'-tetramethyl.

8. The method of claim 6 wherein said water-soluble cationic polymer is provided as a salt.

9. The method of claim 1 wherein said copper-, silver-, and/or zinc-containing biocide is provided to the pool in conjunction with a water-soluble anionic or cationic polymeric sequestering agent and an organic sequestering agent differing in composition from said water-soluble anionic or cationic polymeric sequestering agent.

10. The method of claim 1 wherein said water-soluble anionic or cationic polymeric sequestering agent has a molecular weight of between about 500 Da and about 20,000,000 Da.

11. The method of claim 10 wherein said water-soluble anionic or cationic polymeric sequestering agent has a molecular weight of between about 1,000 Da and about 5,000,000 Da.

12. The method of claim 11 wherein said water-soluble anionic or cationic polymeric sequestering agent has a molecular weight of between about 1,000 Da and about 1,500,000 Da.

13. A method of extending the useful life of a copper-, silver-, and/or zinc-containing biocide, comprising providing the copper-, silver-, and/or zinc-containing biocide to a pool in conjunction with a water-soluble anionic or cationic polymeric sequestering agent effective to sequester at least some of the copper, silver, and/or zinc; wherein said copper, silver, and/or zinc is present in the pool water in an amount ranging from 0.025 ppm to 0.7 ppm, and the ratio of "anionic or cationic polymeric sequestering agent" to "copper, silver, and/or zinc" in the pool water is between 0.7:1 and 4.7:1.

14. The method of claim 13 wherein said water-soluble anionic or cationic polymeric sequestering agent is a water-soluble anionic polymer.

15. The method according to claim 14 wherein said water-soluble anionic polymer is a member selected from the group consisting of polyacrylic acid, polymethacrylic acid, polyvinyl sulfonic acid, polystyrene sulfonic acids, polymaleic acid, polyaspartic acid and polyphosphino carboxylic acid.

16. The method of claim 13 wherein said water-soluble anionic or cationic polymeric sequestering agent is a water-soluble cationic polymer.

17. The method of claim 16 wherein said water-soluble cationic polymer is a member selected from the group consisting of poly[oxyethylene-(dimethylimino) ethylene-(dimethylimino) ethylene dichloride], polyethylene imine, diallyl dimethyl ammonium chloride, polyacrylamide derivatives, polyamines, polyvinyl amine, chitosan, polyethylene amine, polymers of 1,6-hexanediamine-N,N,N',N'-tetramethyl.

18. The method of claim 13 wherein said copper-, silver-, and/or zinc-containing biocide is provided to the pool in conjunction with a water-soluble anionic or cationic polymeric sequestering agent and an organic sequestering agent differing in composition from said water-soluble anionic or cationic polymeric sequestering agent.

19. The method of claim 13 wherein said water-soluble anionic or cationic polymeric sequestering agent comprises between about 10% and about 50%, by weight of the copper-, silver-, and/or zinc-containing biocide and water-soluble anionic or cationic polymeric sequestering agent added to the pool.

20. The method of claim 13 wherein said water-soluble anionic or cationic polymeric sequestering agent has a molecular weight of between about 500 Da and about 20,000,000 Da.

21. The method of claim 20 wherein said water-soluble anionic or cationic polymeric sequestering agent has a molecular weight of between about 1,000 Da and about 5,000,000 Da.

22. The method of claim 21 wherein said water-soluble anionic or cationic polymeric sequestering agent has a molecular weight of between about 1,000 Da and about 1,500,000 Da.

\* \* \* \* \*